US011980190B2

(12) United States Patent
Comby et al.

(10) Patent No.: US 11,980,190 B2
(45) Date of Patent: May 14, 2024

(54) MICROBIAL STRAINS FOR BIOLOGICALLY CONTROLLING FUSARIUM HEAD BLIGHT

(71) Applicant: Establissements J. Soufflet, Nogent sur Seine (FR)

(72) Inventors: Morgane Anne Laure Comby, Boisleux-au-Mont (FR); Camille Simone Madeleine Profizi, Nantes (FR); Fabienne Louise Madeleine Baillieul, Taissy (FR); Joëlle Marie Dupont, Paris (FR); Mathilde Marie Charlotte Robineau, Bourgogne (FR)

(73) Assignee: Establissements J. Soufflet, Nogent sur Seine (FR)

( * ) Notice: Subject to any disclaimer, the term of this patent is extended or adjusted under 35 U.S.C. 154(b) by 1486 days.

(21) Appl. No.: 16/306,918

(22) PCT Filed: Jun. 6, 2017

(86) PCT No.: PCT/EP2017/063741
§ 371 (c)(1),
(2) Date: Dec. 4, 2018

(87) PCT Pub. No.: WO2017/211848
PCT Pub. Date: Dec. 14, 2017

(65) Prior Publication Data
US 2019/0133136 A1 May 9, 2019

(30) Foreign Application Priority Data
Jun. 6, 2016 (EP) .................................... 16305659

(51) Int. Cl.
| | |
|---|---|
| *A01H 17/00* | (2006.01) |
| *A01N 63/27* | (2020.01) |
| *A01N 63/30* | (2020.01) |
| *C12N 1/14* | (2006.01) |
| *C12N 1/20* | (2006.01) |
| *C12R 1/38* | (2006.01) |
| *C12R 1/645* | (2006.01) |

(52) U.S. Cl.
CPC ............ *A01N 63/27* (2020.01); *A01H 17/00* (2013.01); *A01N 63/30* (2020.01); *C12N 1/145* (2021.05); *C12N 1/205* (2021.05); *C12R 2001/38* (2021.05); *C12R 2001/645* (2021.05)

(58) Field of Classification Search
CPC ................................. A01H 17/00; A01N 63/27
See application file for complete search history.

(56) References Cited

U.S. PATENT DOCUMENTS

| 7,601,346 B1 | 10/2009 | Schisler et al. |
| 2010/0093538 A1* | 4/2010 | Gnanamanickam ... C12N 1/205 504/117 |
| 2015/0327556 A1 | 11/2015 | Brahm et al. |

FOREIGN PATENT DOCUMENTS

| EP | 0257756 A2 | 3/1988 |
| EP | 0257756 A3 | 3/1990 |

OTHER PUBLICATIONS

Selvakumar et al World Journal of Microbiology and Biotechnology vol. 27, pp. 1129-1135 (Year: 2011).*
Yoshida et al Microb. Ecol. vol. 64, pp. 214-225 (Year: 2012).*
Selvakumar et al World J. Microbiol. Biotechnol. vol. 27, pp. 1129-1135 (Year: 2011).*
Wachowska, U. et al., "Microorganisms as Biological Control Agents Against Fusarium Pathogens in Winter Wheat," Polish Journal of Environmental Studies, vol. 22, No. 2, Jan. 1, 2013, pp. 591-597.
Yoshida, S. et al., "Specificity of Pseudomonas Isolates on Healthy and Fursarium Head Blight-Infected Spikelets of Wheat Heads," Microbial Ecology, Springer Science & Business Media, vol. 64, No. 1, Feb. 8, 2012, pp. 214-225.
Comby, M. et al., "Spatial and Temporal Variation of Cultivable Communities of Co-Occurring Endophytes and Pathogens in Wheat," Frontiers in Microbiology, vol. 7, Mar. 31, 2016, pp. 1-16.
Schisler, D. et al., "Population Dynamics of the Fusarium Head Blight Biocontrol Agent Cryptococcus Flavescens OH 182.9 on Wheat Anthers and Heads," Biological Control, vol. 70, Dec. 5, 2013, pp. 17-27.
Szentes, S. et al., "Selection and Evaluation of Potential Biocontrol Rhizobacteria from a Raised Bog Environment," Crop Protection, vol. 52, Jun. 19, 2013, pp. 116-124.
Selvakumar, G. et al., "Pseudomonas Lurida M2RH3 (MTCC 9245), A Psychrotolerant Bacterium from the Uttarakhand Himalayas, Solubilizes Phosphate and Promotes Wheat Seedling Growth," World Journal of Microbiology and Biotechnology, vol. 27, No. 5, Sep. 18, 2010, pp. 1129-1135.
Brum, M.C.P. et al., "Endophytic Fungi from *Vitis labrusca* L. ('Niagara Rosada') and its Potential for the Biological Control of Fusarium Oxysporum," Genetics and Molecular Research, vol. 11, No. 4, Dec. 6, 2012, pp. 4187-4197.
Floudas, D. et al., "Revisiting the Taxonomy of Phanerochaete (Polyporales, Basidiomycota) Using a Four Gene Dataset and Extensive ITS Sampling," Fungal Biology, vol. 119, No. 8, Aug. 1, 2015, pp. 679-719.
Kageyama, S.A. et al., "Diversity, Function and Potential Applications of the Root-Associated Endophytes," Springer-Verlag Berlin Heidelberg, Jan. 1, 2008, pp. 29-57.
European Search Report and Written Opinion for European U.S. Appl. No. 16/305,659, filed Oct. 13, 2016, 18 pp.

(Continued)

*Primary Examiner* — David H Kruse
(74) *Attorney, Agent, or Firm* — Soquel Group LLC

(57) ABSTRACT

The present invention concerns the use of the microorganisms species *Pseudomonas trivialis, Pseudomonas lurida, Phaeophlebiopsis* sp., *Periconia macrospinosa* for preventing and/or treating *Fusarium* head blight in cereal plants and/or grains.

8 Claims, 3 Drawing Sheets

(56) References Cited

OTHER PUBLICATIONS

Partial European Search Report for European Application No. 16/305,659, filed Aug. 18, 2016, 7 pp.
PCT International Search Report for International Application No. PCT/EP2017/063741, dated Nov. 30, 2017, 8 pp.
PCT Written Opinion of the International Searching Authority for International Application No. PCT/EP2017/063741, dated Nov. 30, 2017, 9 pp.
Baffoni, et al., "Microbial inoculants for the biocontrol of *Fusarium* spp. in durum wheat", BMC Microbiology, 1Department of Agricultural Sciences, University of Bologna, 2015, 10 pages.
I. Bujold and T. C. Paulitz, Macdonald Campus of McGill University, Ste. Anne de Bellevue, QC, Canada; and O. Carisse, Agriculture and Agri-Food Canada, St. Jean sur Richelieu, QC, Canada, Plant Disease/Sep. 2001, 8 pages.
George C. Carroll and Fanny E. Carroll, "Studies on the incidence of coniferous needle endophytes in the Pacific Northwest", Department of Biology, University of Oregon, 1978, 10 pages.
A. Champeil, T. Doré, J.F. Fourbet, "Fusarium head blight: epidemiological origin of the effects of cultural practices on head blight attacks and the production of mycotoxins by Fusarium in wheat grains", Elsevier, Science Direct, Plant Science 2004, 27 pages.
Javier Collado, et al., "High-throughput culturing of fungi from plant litter by a dilution-to-extinction technique", 2007 Merck & Co., Inc., Journal Compilation, Federation of European Microbiological Societies Published by Blackwell Publishing Ltd., 13 pages.
Christopher A. Dunlap, et al., "Genomic analysis and secondary metabolite production in Bacillus amyloliquefaciens AS 43.3: A biocontrol antagonist of Fusarium head blight", Elsevier, Biological Control 64, 2013, 10 pages.
George Carroll, "Fungal Endophytes in Stems and Leaves: From Latent Pathogen to Mutualistic Symbiont", Ecology, vol. 69, No. 1, 1988 by the Ecological Society of America, 8 pages.
Jeannie Gilbert & Steve Haber, "Overview of some recent research developments in fusarium head blight of wheat", Canadian Journal of Plant Pathology, Mar. 12, 2013, 27 pages.
Mt Kheng Goh, et al., "Effects of abiotic factors and biocontrol agents on chlamydospore formation in Fusarium graminearum and Fusarium sporotrichioides", Biocontrol Science and Technology, vol. 19, No. 2, 2009, 18 pages.
N.I. Khan, et al., "Field testing of antagonists of Fusarium head blight incited by Gibberella zeae", Elsevier, Science Direct, Biological Control 29, 2004, 11 pages.
Laura Luongo, et al., "Potential of fungal antagonists for biocontrol of *Fusarium* spp. in wheat and maize through competition in crop debris", Biocontrol Science and Technology, Jan. 18, 2007, 15 pages.
Wilmar Corio da Luz, et al., "Biological Control of Fusarium graminearum", Chapter 14, 2003, pp. 381-394.
F. Matarese, et al., "Biocontrol of Fusarium head blight: interactions between Trichoderma and mycotoxigenic Fusarium", Microbiology, 2012 SGM, 9 pages.
Á. Mesterházy, et al., "Influence of Wheat Cultivar, Species of *Fusarium*, and Isolate Aggressiveness on the Efficacy of Fungicides for Control of Fusarium Head Blight", The American Phytopathological Society, Plant Disease, Sep. 2003, 9 pages.
Carloalberto Petti, et al., "Lipid transfer proteins and protease inhibitors as key factors in the priming of barley responses to Fusarium head blight disease by a biocontrol strain of Pseudomonas fluorescens", Funct Integr Genomics, 2010, Springer, 9 pages.
D. A. Schisler, et al., "Greenhouse and Field Evaluation of Biological Control of Fusarium Head Blight on Durum Wheat", Plant Disease / vol. 86 No. 12, Jul. 2002, 7 pages.
Barbara Schulz, et al., "Endophyte-Host Interactions. II. Defining Symbiosis of the Endophyte—Host Interaction", Second International Congress of Symbiosis, Symbiosis, 25 (1998) pp. 213-227, Balaban, Philadelphia/Rehovot.
Unterseher, Martin, "Dilution-to-extinction cultivation of leaf-inhabiting endophytic fungi in beech (*Fagus sylvatica* L.)—Different cultivation techniques influence fungal biodiversity assessment", Elsevier, British Mycological Society, 2009, 10 pages.
Rytas Vilgalys, et al., "Rapid Genetic Identification and Mapping of Enzymatically Amplified Ribosomal DNA from Several *Cryptococcus* Species", Journal of Bacteriology, Aug. 1990, pp. 4238-4246.
Rytas Vilgalys, et al., "Ancient and recent patterns of geographic speciation in the oyster mushroom Pleurotus revealed by phylogenetic analysis of ribosomal DNA sequences", Proc. Nati. Acad. Sci. USA vol. 91, pp. 4599-4603, May 1994 Evolution.
T. J. White, et al., "Amplification and Direct Sequencing of Fungal Ribosomal RNA Genes for Phylogenetics", PCR Protocols: A Guide to Methods and Applications, 1990, 8 pages.
Kenneth H. Wilson, et al., "Amplification of Bacterial 16S Ribosomal DNA with Polymerase Chain Reaction", Journal of Clinical Microbiology, Sep. 1990, American Society for Microbiology, pp. 1942-1946.
A.G. Hue, et al., "Biological control of fusarium head blight of wheat with Clonostachys rosea strain ACM941", Canadian Journal of Plant Pathology, 12 pages, 2009.
J. C. Zadoks, et al., "A decimal code for the growth stages of cereals", Weed Research, 1974, vol. 14, 8 pages.

* cited by examiner

MICROBIAL STRAINS FOR BIOLOGICALLY CONTROLLING FUSARIUM HEAD BLIGHT

The present invention concerns the prevention and/or treatment of *Fusarium* head blight in cereal plants and/or grains.

*Fusarium* head blight (FHB), also known as scab of wheat, is one of the most important diseases on wheat and barley crops worldwide, leading to important yield losses and reduced market prices due to poor quality of FHB-infected grains. The disease is caused by phytopathogenic fungi such as *Microdochium nivale* and several species of *Fusarium*. Among those species, *F. graminearum* (teleomorph: *Gibberella zeae*) and *F. culmorum* are the most prevalent and most pathogenic (Champeil et al., Plant Science 166, 1389-415, 2004). *Fusarium* spp. are responsible for the production of mycotoxins during the colonization of grain, such as trichothecenes deoxynivalenol (DON) or nivalenol (NIV) and zearalenone, leading to animals and humans health concerns. In recent decades, FHB has re-emerged as a disease of major significance, with recent outbreaks occurring all over the world. Climatic factors greatly influence the incidence and severity of FHB. In the actual context of climate change, a new repartition map of the fungal species responsible for the disease is ongoing and FHB might therefore become a problem in world areas non-affected until now. Anthesis is the most crucial time for the development of FHB, thus the critical stage for the infection is relatively short. The disease can destroy the whole wheat crop only weeks before harvest, by infecting developing heads at flowering.

Consistently effective control measures against FHB are lacking. No fully resistant cultivar exists so far and the disease control is primarily based on the use of fungicides along with cultural control techniques, such as tillage practices and crop rotation, to reduce the inoculum (Gilbert & Haber, *Canadian Journal of Plant Pathology* 35, 149-74, 2013). Good levels of control can be achieved with fungicides but their efficacy seems to depend on the fungal species involved, different species being capable of various responses towards a particular fungicide (Mesterhazy et al., *Plant Disease* 87, 1107-15, 2003). This is a critical point for the control of FHB involving a complex of pathogenic fungi which can vary in virulence, leading to contradictory results of fungicide efficacy. Moreover, the use of fungicides leads to environmental and health concerns.

In the present context of reduction of pesticides use, biological control is promising and offers an additional strategy to be used as part of an integrated management of FHB. The use of some biological control agents has been documented as a potential alternative to control *Fusarium* spp. regarding tests conducted in vitro, in planta in controlled conditions or even under field conditions. *Bacillus subtilis* and *Bacillus amyloliquefaciens* (Goh et al., *Biocontrol Sci. Technol.* 19, 151-167, 2009, Baffoni et al., *BMC Microbiol.* 15, 242, 2015, Dunlap et al., *Biological Control* 64, 166-75, 2013), *Pseudomonas fluorescens* and *Pseudomonas chlororaphis*, (Petti et al., *Functional and Integrative Genomics* 10, 619-27, 2010; Hu et al., *Phytopathology* 104, 1289-97, 2014), *Trichoderma* (Matarese et al., *Microbiology* 158, 98-106, 2012) and *Cryptococcus* (Schisler et al., *Biological Control* 70, 17-27, 2014) have been the most commonly investigated microorganisms for the control of *Fusarium*. Yoshida et al (in *Microbial Ecology*, 64, no. 1, 8, 214-225, 2012) describe the use of several *Pseudomonas* species divided in clusters against wheat FHB. One cluster (cluster C) comprises isolates of which the tested isolates showed good affinity with *Fusarium* propagules, and showed a strong growth inhibitory activity against this pathogen. This cluster comprises various species including *Pseudomonas poae*. The other members of the cluster are bacteria of the genus *Pseudomonas* whose species are not specified.

However, consistent efficacy of FHB biocontrol over time and across location is difficult to achieve (Khan et al., *Biological Control* 29, 245-55, 2004).

There is thus a need for new biological control agents capable of preventing and/or treating FHB, capable in particular of inhibiting both *F. graminearum* and *F. culmorum*.

By studying the plants' microbiote, the inventors have now identified four microorganisms species capable of inhibiting efficiently *F. graminearum* and *F. culmorum*. These microorganisms are effective for the suppression and control of FHB in cereals, particularly in wheat and barley. The four microorganisms are the bacteria *Pseudomonas trivialis* (PsTri), in particular the strains PsTri1, PsTri2, PsTri3, PsTri4, PsTri5 and PsTri6, and *Pseudomonas lurida* (PsLu), in particular the strains PsLu1, PsLu2 and PsLu3, and the fungi *Phaeophlebiopsis* sp. (PS), in particular the strain PS1, and *Periconia macrospinosa* (PM), in particular the strains PM1 and PM2. These microorganisms were identified from a pool of 758 microbial strains obtained from roots and aerial organs of wheat, including leaves, stems, anthers, glumes, rachis, and kernels. Initial identification of specific colonists for further study was based on the ability of a colonist to reduce the severity of FHB by reducing mycelial growth and/or inhibiting *Fusarium* spp. spores germination. The four antagonists species selected in this manner were particularly effective in reducing FHB severity in in vitro assays. Additionally, *Pseudomonas trivialis*, in particular the strain PsTri3, *Pseudomonas lurida*, in particular the strain PsLu3, and *Phaeophlebiopsis* sp., in particular the strain PS1, were particularly effective in reducing *F. graminearum* infection in in planta assays.

In Yoshida et al., a P-292 isolate belonging to cluster C from a *F. graminearum*-infected Yuki-chikara wheat spikelet was identified as containing 16S RNA with 100% homology to *Pseudomonas trivialis* AJ492831 and *Pseudomonas poae* AJ4922829, both species being genetically very close. However, *Pseudomonas trivialis* AJ492831 is not one of the isolates tested.

Moreover, isolates showing a strong inhibitory activity of *Fusarium* growth are not identified as strains of *Pseudomonas trivialis*.

The present invention thus concerns the use of at least one plant-associated microorganism selected from the group consisting of *Pseudomonas trivialis* (PsTri), *Pseudomonas lurida* (PsLu), *Periconia macrospinosa* (PM), *Phaeophlebiopsis* sp. (PS), and combinations thereof, in the prevention and/or treatment of *Fusarium* head blight in cereal plants and/or cereal grains.

Another object of the present invention is a method for preventing and/or treating *Fusarium* head blight in a cereal plant and/or grain, comprising a step of applying an effective amount of at least one plant-associated microorganism to said plant, to the soil around said plant or to the seed or grain of said plant, wherein said at least one plant-associated microorganism is selected from the group consisting of *Pseudomonas trivialis* (PsTri), *Pseudomonas lurida* (PsLu), *Phaeophlebiopsis* sp. (PS), *Periconia macrospinosa* (PM) and combinations thereof.

The present invention also concerns a phytosanitary composition comprising at least one plant associated microorganism selected from the group consisting of *Pseudomonas*

*trivialis* (PsTri), *Pseudomonas lurida* (PsLu), *Phaeophlebiopsis sp.* (PS), *Periconia macrospinosa* (PM), natural variants thereof, and combinations thereof, in an agronomically acceptable carrier, in particular for the prevention and/or treatment of *Fusarium* head blight in cereal plants and/or cereal grains.

The invention also concerns a plant-associated microorganism selected from:

(i) the *Pseudomonas trivialis* strain PsTri1 deposited under the Budapest Treaty with the Centralbureau voor Schimmelcultures (CBS, Uppsalalaan 8, 3584 CT Utrecht, Netherlands) on May 31, 2016 under Accession number CBS 141 431, (ii) the *Pseudomonas trivialis* strain PsTri2 deposited under the Budapest Treaty with the Centralbureau voor Schimmelcultures (CBS, Uppsalalaan 8, 3584 CT Utrecht, Netherlands) on May 31, 2016 under Accession number CBS 141 432, (iii) the *Pseudomonas trivialis* strain PsTri3 deposited under the Budapest Treaty with the Centralbureau voor Schimmelcultures (CBS, Uppsalalaan 8, 3584 CT Utrecht, Netherlands) on Apr. 28, 2016 under Accession number CBS 141 433, (iv) the *Pseudomonas trivialis* strain PsTri4 deposited under the Budapest Treaty with the Centralbureau voor Schimmelcultures (CBS, Uppsalalaan 8, 3584 CT Utrecht, Netherlands) on Apr. 28, 2016 under Accession number CBS 141 434, (v) the *Pseudomonas trivialis* strain PsTri5 deposited under the Budapest Treaty with the Centralbureau voor Schimmelcultures (CBS, Uppsalalaan 8, 3584 CT Utrecht, Netherlands) on Apr. 28, 2016 under Accession number CBS 141 435, (vi) the *Pseudomonas trivialis* strain PsTri6 deposited under the Budapest Treaty with the Westerdjik Fungal Biodiversity Institute (CBS, Uppsalalaan 8, 3508 AD Utrecht, Netherlands) on May 15, 2017 under Accession number CBS 142 248, (vii) the *Pseudomonas lurida* strain PsLu1 deposited under the Budapest Treaty with the Centralbureau voor Schimmelcultures (CBS, Uppsalalaan 8, 3584 CT Utrecht, Netherlands) on May 31, 2016 under Accession number CBS 141 436, (viii) the *Pseudomonas lurida* strain PsLu2 deposited under the Budapest Treaty with the Centralbureau voor Schimmelcultures (CBS, Uppsalalaan 8, 3584 CT Utrecht, Netherlands) on Apr. 28, 2016 under Accession number CBS 141 437, (ix) the *Pseudomonas lurida* strain PsLu3 deposited under the Budapest Treaty with the Centralbureau voor Schimmelcultures (CBS, Uppsalalaan 8, 3584 CT Utrecht, Netherlands) on Apr. 28, 2016 under Accession number CBS 141 438, (x) the *Phaeophlebiopsis sp.* strain PS1 deposited under the Budapest Treaty with the Centralbureau voor Schimmelcultures (CBS, Uppsalalaan 8, 3584 CT Utrecht, Netherlands) on Apr. 28, 2016 under Accession number CBS 141 441, (xi) the *Periconia macrospinosa* strain PM1 deposited under the Budapest Treaty with the Centralbureau voor Schimmelcultures (CBS, Uppsalalaan 8, 3584 CT Utrecht, Netherlands) on Apr. 28, 2016 under Accession number CBS 141 439

(xii) the *Periconia macrospinosa* strain PM2 deposited under the Budapest Treaty with the Centralbureau voor Schimmelcultures (CBS, Uppsalalaan 8, 3584 CT Utrecht, Netherlands) on Apr. 28, 2016 under Accession number CBS 141 440, or (xiii) a natural variant of the strain PsTri1, PsTri2, PsTri3, PsTri4, PsTri5, PsTri6, PsLu1, PsLu2, PsLu3, PS1, PM1 or PM2, providing a protection score against FHB at least equal to that obtained under the same conditions with its reference strain.

The invention also concerns a plant-associated microorganism which is the *Clonostachys rosea* strain CR deposited under the Budapest Treaty with the Centralbureau voor Schimmelcultures (CBS, Uppsalalaan 8, 3584 CT Utrecht, Netherlands) on Apr. 28, 2016 under Accession number CBS 141 426, and natural variants thereof providing a protection score against FHB at least equal to that obtained under the same conditions with its reference strain.

DETAILED DESCRIPTION OF THE INVENTION

*Fusarium* Head Blight

As intended herein, "*Fusarium* head blight", "FHB", "*Fusarium* ear blight" or "scab" are used interchangeably and refer to a disease associated to a complex of species involving two genera of phytopathogenic fungi: *Fusarium* and *Microdochium*. As well-known from the skilled person, in cereals, FHB is usually caused by a set of different *Fusarium* species, with different lifestyles and different types of mycotoxins produced. Within the *Fusarium graminearum* species complex, which presently includes 16 species, *F. graminearum sensu stricto* and *F. culmorum* are the most dominant pathogens causing head blight on wheat and other cereals worldwide, the species *F. graminearum* being the main species in most cases because of its adaptability to a broad range of temperature and to the rapid propagation of the infection.

Other frequently detected species are *F. cerealis, F. poae, F. avenaceum, F. langsethiae, F. tricinctum, F. sporotrichioides*, and the non-toxigenic species *Microdochium nivale* and *M. majus*.

In wheat, *Fusarium* infects the head (hence the name "*Fusarium* head blight") and causes the kernels to shrivel up and become chalky white. Additionally, the fungus can produce mycotoxins that further reduce the quality of the kernel. Infected florets (especially the outer glumes) typically become slightly darkened and oily in appearance. Conidiospores are typically produced in sporodochia, which gives the spike a bright pinkish color. Infected kernels may be permeated with mycelia and the surface of the florets totally covered by white, matted mycelia.

In the context of the invention, the term "*Fusarium*" is intended to include both the sexual (teleomorphic) stage of this organism and also the asexual (anamorphic) stage, also referred to as the perfect and imperfect fungal stages, respectively. For example, the anamorphic stage of *Gibberella zeae* corresponds to *Fusarium graminearum*. In one embodiment, *Fusarium* is *Fusarium roseum*, encompassing the species *Fusarium graminearum* and *Fusarium culmorum*. The term *Fusarium roseum*, although belonging to the ancient taxonomy, is still currently used and its definition may be found in Leslie and Summerell, The *Fusarium* Laboratory Manual, 2006.

In a preferred embodiment, FHB is caused by *Fusarium graminearum*.

In another preferred embodiment, FHB is caused by *Fusarium culmorum*, preferably *Fusarium culmorum* strain Fc37 available at the CBS collection under accession number CBS120103.

Plant-Associated Microorganisms

The terms "microorganisms" and "biological control agents" as intended herein are used interchangeably and refer to bacteria as well as fungi.

The microorganisms according to the invention are typically isolated from Apache wheat plants and Caphorn wheat plants and were typically collected at heading (GrowthStage 59 (GS 59), according to the code defined by Zadoks et al., 1974, Weed Research, Volume 14, Issue 6, pages 415-421), flowering (GS 61-69) and/or mealy ripe (GS 77-79).

Zadoks growth scale is a 0-99 scale of development that is recognised internationally for research, advisory work and farm practice.

The Zadok's growth scale is based on ten principal cereal growth stages:

0—Germination
1—Seeding growth
2—Tillering
3—Stem elongation
4—Booting
5—Awn emergence
6—Flowering (anthesis)
7—Milk development
8—Dough development
9—Ripening Each primary growth stage is divided into 10 secondary stages, extending the scale from 00 to 99. The early growth stages (1, 2 and 3) are referred to most frequently. The scale does not run chronologically from GS 00 to GS 99. For example, when the crop reaches three fully unfolded leaves (GS 13) it begins to tiller (GS 20), before it has completed four, five or six fully unfolded leaves (GS 14, 15, 16).

Preferably, the microorganisms used in the context of the invention are isolated from aerial organs of a cereal plant.

The microorganisms according to the invention are "plant-associated" microorganisms. Such microorganisms can be endophytes, epiphytes or saprophytes.

As intended herein, the terms "endophytic microorganism", or "endophyte" are used interchangeably and refer to a microorganism naturally occurring within any plants organs without causing any damage to its host.

As intended herein, the term "epiphytic microorganism" or "epiphyte" refers to a microorganism living upon, or attached to, a living plant, including any organs of said plant.

As intended herein, the term "saprophytic microorganism" or "saprophyte" refers to a microorganism which does not develop in the living plant and feeds on the waste generated within it.

In one preferred embodiment, the plant-associated microorganism belongs to the *Pseudomonas trivialis* species.

*Pseudomonas trivalis* (PsTri) is a fluorescent, Gram-negative bacterium of the *Pseudomonaceae* genus, which was initially isolated from the phyllosphere of grasses. The present inventors more particularly identified 6 new strains of *Pseudomonas trivalis* from inner tissues of Apache wheat plants and Caphorn wheat plants: the *Pseudomonas trivialis* strains PsTri1, PsTri2, PsTri3, PsTri4, PsTri5, and PsTri6.

The *Pseudomonas trivialis* strain PsTri1 was deposited under the Budapest Treaty with the Centralbureau voor Schimmelcultures (CBS, Uppsalalaan 8, 3584 CT Utrecht, Netherlands) on May 31, 2016 under Accession number CBS 141 431.

The *Pseudomonas trivialis* strain PsTri2 was deposited under the Budapest Treaty with the Centralbureau voor Schimmelcultures (CBS, Uppsalalaan 8, 3584 CT Utrecht, Netherlands) on May 31, 2016 under Accession number CBS 141 432.

The *Pseudomonas trivialis* strain PsTri3 was deposited under the Budapest Treaty with the Centralbureau voor Schimmelcultures (CBS, Uppsalalaan 8, 3584 CT Utrecht, Netherlands) on Apr. 28, 2016 under Accession number CBS 141 433.

The *Pseudomonas trivialis* strain PsTri4 was deposited under the Budapest Treaty with the Centralbureau voor Schimmelcultures (CBS, Uppsalalaan 8, 3584 CT Utrecht, Netherlands) on Apr. 28, 2016 under Accession number CBS 141 434.

The *Pseudomonas trivialis* strain PsTri5 was deposited under the Budapest Treaty with the Centralbureau voor Schimmelcultures (CBS, Uppsalalaan 8, 3584 CT Utrecht, Netherlands) on Apr. 28, 2016 under Accession number CBS 141 435.

The *Pseudomonas trivialis* strain PsTri6 was deposited under the Budapest Treaty with the Westerdjik Fungal Biodiversity Institute (CBS, Uppsalalaan 8, 3508 AD Utrecht, Netherlands) on May 15, 2017 under Accession number CBS 142 248.

Accordingly, in a particular embodiment, the plant-associated microorganism is selected from the group consisting of *Pseudomonas trivialis* strains PsTri1, PsTri2, PsTri3, PsTri4, PsTri5, PsTri6, natural variants thereof and combinations thereof. More preferably, the plant-associated microorganism is selected from the group consisting of *Pseudomonas trivialis* strains PsTri1, PsTri2, PsTri3, PsTri4, PsTri5, PsTri6 and combinations thereof. Even more preferably, the plant-associated microorganism is *Pseudomonas trivialis* strain PsTri3 or a natural variant thereof.

In another embodiment, the plant-associated microorganism belongs to the *Pseudomonas lurida* species.

*Pseudomonas lurida* (PsLu) is a fluorescent, Gram-negative bacterium of the *Pseudomonadaceae* genus, which was initially isolated from the phyllosphere of grasses. The present inventors more particularly identified 3 new strains of *Pseudomonas lurida* from inner tissues of Apache wheat plants and Caphorn wheat plants: the *Pseudomonas lurida* strains PsLu1, PsLu2 and PsLu3.

The *Pseudomonas lurida* strain PsLu1 was deposited under the Budapest Treaty with the Centralbureau voor Schimmelcultures (CBS, Uppsalalaan 8, 3584 CT Utrecht, Netherlands) on May 31, 2016 under Accession number CBS 141 436.

The *Pseudomonas lurida* strain PsLu2 was deposited under the Budapest Treaty with the Centralbureau voor Schimmelcultures (CBS, Uppsalalaan 8, 3584 CT Utrecht, Netherlands) on Apr. 28, 2016 under Accession number CBS 141 437.

The *Pseudomonas lurida* strain PsLu3 was deposited under the Budapest Treaty with the Centralbureau voor Schimmelcultures (CBS, Uppsalalaan 8, 3584 CT Utrecht, Netherlands) on Apr. 28, 2016 under Accession number CBS 141 438.

Accordingly, in a particular embodiment, the plant-associated microorganism is selected from the group consisting of *Pseudomonas lurida* strains PsLu1, PsLu2, PsLu3, natural variants thereof and combinations thereof. More preferably, the plant-associated microorganism is selected from the group consisting of *Pseudomonas lurida* strains PsLu1, PsLu2, PsLu3 and combinations thereof. Even more preferably, the plant-associated microorganism is *Pseudomonas lurida* strain PsLu3 or a natural variant thereof.

In another particular embodiment, the plant-associated microorganism is selected from the group consisting of *Pseudomonas trivialis* strains PsTri1, PsTri2, PsTri3, PsTri4, PsTri5, PsTri6, *Pseudomonas lurida* strains PsLu1, PsLu2, PsLu3, natural variants thereof and combinations thereof. More preferably, the plant-associated microorganism is selected from the group consisting of *Pseudomonas trivialis* strains PsTri1, PsTri2, PsTri3, PsTri4, PsTri5, PsTri6, *Pseudomonas lurida* strains PsLu1, PsLu2, PsLu3 and combinations thereof.

Even more preferably, the plant-associated microorganism is selected from the group consisting of *Pseudomonas trivialis* strain PsTri3 and *Pseudomonas lurida* strain PsLu3, and combinations thereof.

In still another embodiment, the plant-associated microorganism belongs to the *Phaeophlebiopsis* sp. species.

*Phaeophlebiopsis* sp. belongs to the diverse order polyporales (Basidiomycetes). The present inventors more particularly identified one new strain of *Phaeophlebiopsis* sp. from inner tissues of Apache wheat plants and Caphorn wheat plants: the *Phaeophlebiopsis* sp. strain PS1.

The *Phaeophlebiopsis* sp. strain PS1 was deposited under the Budapest Treaty with the Centralbureau voor Schimmelcultures (CBS, Uppsalalaan 8, 3584 CT Utrecht, Netherlands) on Apr. 28, 2016 under Accession number CBS 141 441.

Accordingly, in a particular embodiment, the plant-associated microorganism is selected from the group consisting of *Phaeophlebiopsis* sp. strain PS1 and natural variants thereof. More preferably, the plant-associated microorganism is *Phaeophlebiopsis* sp. strain PS1.

In still another embodiment, the plant-associated microorganism belongs to the *Periconia macrospinosa* species.

*Periconia macrospinosa* belongs to the diverse order Pleosporales (Dothideomycetes). It is known as a root-colonizing endophyte. The present inventors more particularly identified two new strains of *Periconia macrospinosa* from inner tissues of Apache wheat plants and Caphorn wheat plants: the *Periconia macrospinosa* strains PM1 and PM2.

The *Periconia macrospinosa* strain PM1 was deposited under the Budapest Treaty with the Centralbureau voor Schimmelcultures (CBS, Uppsalalaan 8, 3584 CT Utrecht, Netherlands) on Apr. 28, 2016 under Accession number CBS 141 439.

The *Periconia macrospinosa* strain PM2 was deposited under the Budapest Treaty with the Centralbureau voor Schimmelcultures (CBS, Uppsalalaan 8, 3584 CT Utrecht, Netherlands) on Apr. 28, 2016 under Accession number CBS 141 440.

Accordingly, in a particular embodiment, the plant-associated microorganism is selected from the group consisting of *Periconia macrospinosa* strains PM1, PM2, natural variants thereof and combinations thereof. More preferably, the plant-associated microorganism is selected from the group consisting of *Periconia macrospinosa* strains PM1, PM2 and the combination thereof. Even more preferably, the plant-associated microorganism is *Periconia macrospinosa* strain PM1 or a natural variant thereof.

In another particular embodiment, the plant-associated microorganism is selected from the group consisting of *Phaeophlebiopsis* sp. strain PS1, *Periconia macrospinosa* strains PM1, PM2, natural variants thereof and combinations thereof. More preferably, the plant-associated microorganism is selected from the group consisting of *Phaeophlebiopsis* sp. strain PS1, *Periconia macrospinosa* strains PM1, PM2 and combinations thereof.

Even more preferably, the plant-associated microorganism is selected from the group consisting of *Phaeophlebiopsis* sp. strain PS1, *Periconia macrospinosa* strain PM1, and combinations thereof.

In another particular embodiment, the plant-associated microorganism is selected from the group consisting of *Pseudomonas trivialis* strains PsTri1, PsTri2, PsTri3, PsTri4, PsTri5, PsTri6, *Pseudomonas lurida* strains PsLu1, PsLu2, PsLu3, *Phaeophlebiopsis* sp. strain PS1, *Periconia macrospinosa* strains PM1, PM2, natural variants thereof and combinations thereof. More preferably, the plant-associated microorganism is selected from the group consisting of *Pseudomonas trivialis* strains PsTri1, PsTri2, PsTri3, PsTri4, PsTri5, PsTri6, *Pseudomonas lurida* strains PsLu1, PsLu2, PsLu3, *Phaeophlebiopsis* sp. strain PS1, *Periconia macrospinosa* strains PM1, PM2, and combinations thereof.

Still preferably, the plant-associated microorganism is selected from the group consisting of *Pseudomonas trivialis* strain PsTri3, *Pseudomonas lurida* strain PsLu3, *Phaeophlebiopsis* sp. strain PS1, *Periconia macrospinosa* strain PM1, natural variants thereof and combinations thereof. Even more preferably, the plant-associated microorganism is selected from the group consisting of *Pseudomonas trivialis* strain PsTri3, *Pseudomonas lurida* strains PsLu3, *Phaeophlebiopsis sp*. strain PS1, *Periconia macrospinosa* strain PM1 and combinations thereof.

As intended herein, the term "natural variant" refers to a strain preferably obtained without any genetic manipulation, from a natural reference strain, the said obtained strain being able to prevent and/or treat *Fusarium* head blight on cereal plants and/or grains, in particular to inhibit *Fusarium culmorum* and/or *Fusarium graminearum* growth in dual culture assays and/or on wheat spikelets, at the same level as the reference natural strain. The natural variant may thus be obtained by crossing and/or hybridization of *Pseudomonas trivialis, Pseudomonas lurida, Periconia macrospinosa* or *Phaeophlebiopsis* sp. strains and/or by spontaneous mutation and/or by random mutagenesis, such as following exposure to stress conditions, a UV treatment or treatment with other mutagen agents.

The genetic heritage of a natural variant has preferably not been modified by genetic engineering. The natural variant is preferably not a genetically modified organism. Preferably, the natural variant of *Pseudomonas trivialis* strains PsTri1, PsTri2, PsTri3, PsTri4, PsTri5 or PsTri6, *Pseudomonas lurida* strains PsLu1, PsLu2 or PsLu3, *Phaeophlebiopsis* sp. strain PS1 or *Periconia macrospinosa* strains PM1 or PM2, of the invention allows to reduce, in the conditions described in the Example, FHB severity. In particular, when added to the cereal plant or grain in need thereof, the natural variant preferably provides a protection score against FHB, as defined below, at least equal to that obtained under the same conditions with its reference strain.

The protection score can for example be approached either by the Inhibition Index or the Inhibition Score in in vitro assays, or by the Protection Index in in planta assays.

The Inhibition Index (Ii) can be calculated for the plant-associated microorganism, for its ability to inhibit *Fusarium* growth in in vitro assays. Seven days after inoculation, typically, the growth diameter (ø) of *Fusarium* can be measured, and li can be calculated following the formula:

$$Ii=[(\text{ø}_{Fusarium\ alone}-\text{ø}_{Fusarium\ in\ confrontation\ with\ the\ microorganism})/\text{ø}_{Fusarium\ alone}]\times 100$$

If this Inhibition Index is determined regarding the two species of *Fusarium*, *Fusarium graminearum* and *Fusarium culmorum*, a global Inhibition Score (Is) can typically be determined as the sum of Inhibition Index values towards both *Fusarium* species *Fusarium graminearum* and *Fusarium culmorum*. Depending on the plant-associated microorganism, Is may range from 0 (no inhibition for any species of *Fusarium*) to 200 points, or, in percentage from 0 to 100%. The plant-associated microorganisms according to the invention have typically an Is superior to 30 points, that is to say superior to 15%, preferably superior to 40 points, that is to say superior to 20%, more preferably superior to 50 points, that is to say superior to 25%, more preferably also superior to 60 points, that is to say superior to 30%, even more preferably superior to 70 points, that is to say superior to 35%.

The protection score can be a Protection Index. The inventors have indeed established a rating system in planta on wheat spikelets in Petri dishes to assess the protection provided by the plant-associated microorganism of the invention. This Protection Index can typically be determined 7 days after inoculation of the pathogen, this time being necessary and enough for *Fusarium* to infect control dishes "not pre-treated" and "water-Tween". A scale of visual ratings of symptoms is for example used to evaluate the severity of infection in each spikelet. This scale has typically four levels: level 0=healthy spikelets, level 1=spikelets with early visible necrosis, level 2=spikelets with visible *Fusarium* mycelium, level 3=very infected spikelet with mycelium of *Fusarium* mycelium and presence of sporodochia.

From these scale ratings, a severity index (SI) can typically be calculated using the formula: $SI=(n0*0+n1*1+n2*2+n3*3)/N$ where N is the total number of spikelets by treatment, and n0, n1, n2, n3 is the number of spikelets by treatment with infection levels of 0, 1, 2 or 3 on the rating scale. This severity index therefore translates for each treatment the level of *Fusarium* aggressiveness. The minimum value of the severity index is 0 (obtained when the level 0 of infection is attributed to all the spikelets) and the maximum value is 3 (obtained when the infection level 3 is assigned to all spikelets).

The visual rating of symptoms is typically conducted on wheat at Growth Stage 50-59 according to the code defined by Zadoks et al. Plant-associated microorganism used for those assays can typically be adjusted to $10^6$ conidia $ml^{-1}$ or cfu $ml^{-1}$ of a liquid composition, respectively for fungal or bacterial strains, from −80° C. stock cultures, in sterile water containing Tween 20 (0.1%) and so called "water-Tween".

The Protection Index may then be based on incidence rates of FHB. The incidence rate can be determined as the percentage of infected spikelets, that is to say the percentage of spikelets which were attributed the infection levels 1, 2 or 3 on the ratings scale defined above. This incidence rate typically reflects the ability of attack of *Fusarium*. The Protection Index can then be calculated using the formula:

Protection Index=[(*SINT*−*SIX*)/*SINT*]×100 where SINT corresponds to the severity index obtained for spikelets untreated and inoculated by *F. gramincarum*, and SIX is the severity index obtained for samples submitted to the treatment X before the inoculation of the pathogen.

Preferably, the plant-associated microorganisms used according to the invention have a Protection Index of at least 60%, preferably at least 70%, more preferably of at least 80%, even more preferably of at least 90%.

The plant-associated microorganism defined above can be used in combination with *Clonostachys rosea*.

*Clonostachys rosea* is a fungus species and belongs to the diverse order hypocreales (Bionectriaceae family). It colonizes living plants as an endophyte, digests material in soil as a saprophyte and is also known as a parasite of other fungi and of nematodes. The present inventors more particularly identified a new strain of *Clonostachys rosea* from inner tissues of Apache wheat plants and Caphorn wheat plants: the *Clonostachys rosea* strain CR.

The *Clonostachys rosea* strain CR was deposited under the Budapest Treaty with the Centralbureau voor Schimmelcultures (CBS, Uppsalalaan 8, 3584 CT Utrecht, Netherlands) on Apr. 28, 2016 under Accession number CBS 141 426.

Preferably, the *Clonostachys rosea* used is the *Clonostachys rosea* strain CR or a natural variant thereof, the natural variant preferably providing a protection score against FHB, as defined above, at least equal to that obtained under the same conditions with its reference strain. Still preferably, the *Clonostachys rosea* used is the *Clonostachys rosea* strain CR.

Optimal conditions for the cultivation of the plant-associated microorganisms of this invention, in particular before application, will, of course, depend upon the particular strain. However, by virtue of the conditions applied in the selection process and general requirements of most microorganisms, a person of ordinary skill in the art would be able to determine essential nutrients and conditions.

The plant-associated microorganisms can typically be grown in aerobic liquid and/or solid cultures on media which contain sources of carbon, nitrogen, and inorganic salts that can be assimilated by the microorganism and supportive of efficient cell growth. Preferred carbon sources are hexoses such as glucose, but other sources that are readily assimilated such as amino acids, may be substituted. Many inorganic and proteinaceous materials may be used as nitrogen sources in the growth process. Preferred nitrogen sources are amino acids and urea but others include gaseous ammonia, inorganic salts of nitrate and ammonium, vitamins, purines, pyrimidines, yeast extract, beef extract, proteose peptone, soybean meal, hydrolysates of casein, distiller's solubles, and the like. Among the inorganic minerals that can be incorporated into the nutrient medium are the customary salts capable of yielding calcium, zinc, iron, manganese, magnesium, copper, cobalt, potassium, sodium, molybdate, phosphate, sulfate, chloride, borate, and like ions. Without being limited thereto, use of Potato Dextrose Agar (PDA, AES, 42 g/L) for fungal strains or Plate Count Agar (PCA, AES, 23.5 g/L) for bacterial strains is preferred.

Typically, cell growth can be achieved at temperatures between 1 and 36° C., with the preferred temperature being in the range of 15-30° C., the most preferred temperature being 25° C. The pH of the nutrient medium can vary between 4 and 9, the preferred operating range being pH 6-8. The incubation time may vary between 24 hours and two weeks depending upon the strain. The incubation can be under dark or light exposition depending on the strain.

Prevention and/or Treatment of *Fusarium* Head Blight

The plant-associated microorganisms of the invention are capable of preventing and/or treating *Fusarium* head blight, in particular of inhibiting *Fusarium culmorum* and/or *Fusarium graminearum* growth, in cereal plants and/or grains.

The term "cereal" as used herein is intended to refer to any cereal species that is normally susceptible to FHB. Cereals reported to be susceptible include wheat, barley, oats, and triticale, though wheat and barley are the two crops in which this disease presents a significant economic problem.

In a preferred embodiment of the invention, the cereal is wheat or barley.

More preferably, the cereal is wheat.

The term "cereal plant" refers to any stage of the plant from tillering to ripening.

The terms "seed" or "grain" are used interchangeably and refer to the cereal seed or kernel before tillering or post-harvest.

The plant-associated microorganisms are preferably applied in an amount effective to prevent and/or treat FHB in cereal plants and/or grains.

As used herein, the term "effective amount" refers to an amount of plant-associated microorganism of the invention enabling obtaining a significant effect in the prevention and/or treatment of FHB, in particular compared to the effect observed with a negative control, such as a non-treated plant.

By "prevention" is meant herein the reduction of occurrence of FHB.

By "treatment" is meant herein the disappearance or reduction of the symptoms of FHB and/or the inhibition of *Fusarium* growth and/or reduction of *Fusarium* mycotoxins. In particular, "treatment" preferably refers to inducing an Inhibition Index Ii, as defined above, superior to 15%, preferably superior to 20%, more preferably superior to 25%, even more preferably also superior to 30%, and/or a Protection Index, as defined above, of at least 50%, preferably of at least 60%, also more preferably of at least 70%, also more preferably of at least 80%, even more preferably of at least 90%.

As described in greater detail in the Example below, prevention and/or treatment of FHB may be effected by application of a plant-associated microorganism of the invention to the head (also referred to as seed head) of a cereal plant.

As used herein, the "head" or "seed head" refers to the spike that contains seeds or the progenitors of seeds.

The plant-associated microorganisms can be applied to the seed head preferably at any time after the boot stage (GS 40-49) and before the hard dough stage (GS 87) of cereal development, according to the Zadoks scale, as defined above.

The cereal head is particularly susceptible to infection by *F. graminearum* from the onset of flowering (anthesis) through the soft dough stage of kernel development. Thus, the best time to apply the biological control agents is preferably from the time immediately preceding flowering until as late as the soft dough stage of kernel development. Application of plant-associated microorganisms to heads before flowering have the advantage of allowing plant-associated microorganisms to colonize wheat head parts prior to the wheat head becoming susceptible to infection. Additionally, plant-associated microorganisms can then be well positioned to colonize and protect anthers as they emerge from florets.

In a further embodiment, the plant-associated microorganism may be applied to the cereal grain or to the seed of said cereal plant.

In particular, the plant-associated microorganism may be applied to cereal grains or seeds by seed coating. Coating of the seeds may be performed by any technique well-known from the skilled person.

In particular, the plant-associated microorganism may be applied to cereal grains or seeds after harvesting, in particular during grains or seeds storage. Treatment of the cereal grains or the seeds may be performed by any technique well-known from the skilled person.

In another embodiment, the plant-associated microorganism is applied to the seedling of said cereal plant. Treatment of the seedling may be performed by any technique well-known from the skilled person.

Preferably, the plant-associated microorganism is applied to the leaves, in particular by foliar applying. Such an application mode is easier to implement and combines a direct effect of the plant-associated microorganism against the pathogen agent present on the leaves' surface.

In one embodiment, at least one plant associated microorganism is applied on the leaves prior to hard dough stage of development of said cereal plant.

In a further embodiment, at least one plant associated microorganism is applied to the leaves during flowering of said cereal plant.

In a preferred embodiment, at least one plant associated microorganism is applied to the leaves prior to flowering of said cereal plant.

Alternatively the plant-associated microorganism may be applied on the soil around the plant. Typically, it may be applied within a radius of 25 cm around the plant, preferably within a radius of 20 cm around the plant, more preferably within a radius of 15 cm around the plant preferably, more preferably also within a radius of 10 cm around the plant, even more preferably within a radius of 5 cm around the plant.

The plant-associated microorganism of the invention is preferably applied in the form of propagules.

As intended herein, the term "propagule" refers to any biological entity that gives rise to a bacterial or fungal colony on a suitable isolation medium. Propagules susceptible to be used include cells, conidia, spores, and mycelium pellets. Preferred bacterial propagules are cells. Preferred fungal propagules are spores.

The actual rate of application of the plant-associated microorganism of the invention will preferably vary from $10^1$ to about $10^{13}$ propagules/ml of liquid composition and preferably from $10^2$ to $10^{12}$ propagules/ml of liquid composition, preferably also from $10^3$ to $10^{11}$ propagules/ml of liquid composition, preferably also from $10^4$ to $10^{10}$ propagules/ml of liquid composition, preferably also from $10^5$ to $10^9$ propagules/ml of liquid composition, preferably also from $10^6$ to $10^8$ propagules/ml of liquid composition, preferably also from $10^7$ to $10^8$ propagules/ml of liquid composition.

Preferably, the plant-associated microorganism is applied to achieve substantially uniform contact of at least 50%, preferably at least 60% and even more preferably at least 70% of the wheat head.

If the plant-associated microorganisms are applied as a solid formulation, the rate of application should be controlled to result in a comparable number of viable cells per unit area of cereal head surface as obtained by the aforementioned rates of liquid treatment.

Although the above-mentioned plant-associated microorganisms are effective when used alone, in an optional yet preferred embodiment, they are applied in combination with other known biological control agents for FHB. A variety of other biological control agents are suitable for use herein and include but are not limited to those disclosed by Bujold et al., *Plant Disease* 85, 977-984, 2001; Schisler et al., *Mycotoxins and Food Safety*, Kluwer Academic/Plenum Publishers, New York, pp. 53-69, 2002; da Luz et al., *Fusarium head blight of wheat and barley*, APS Press, St. Paul, Minn., 381-394, 2003; Gilbert & Fernando, *Canadian Journal of Plant Pathology* 26, 1-9, 2004; Schisler et al., U.S. Pat. Nos. 6,562,337 and 6,312,940, and Xue et al., *Canadian Journal of Plant Pathology* 31, 169-79, 2009. Use of the plant-associated microorganisms according to the invention in combination with the microbial antagonist *Clonostachys rosea* as defined above is preferred. These additional biological control agents may be applied with the plant-associated microorganisms of the invention, such as in a mixture, or they may be applied separately or at different times. Preferably, *Clonostachys rosea* strain CR is used at a concentration of from $10^1$ to about $10^{13}$ propagules/ml of liquid composition and preferably from $10^2$ to $10^{12}$ propagules/ml of liquid composition, preferably also from $10^3$ to $10^{11}$ propagules/ml of liquid composition, preferably also from $10^4$ to $10^{10}$ propagules/ml of liquid composition, preferably also from $10^5$ to $10^9$ propagules/ml of liquid composition, preferably also from $10^6$ to $10^8$ propagules/ml of liquid composition, preferably also from $10^7$ to $10^8$ propagules/ml of liquid composition. Preferably, the plant-associated microorganism is applied as a liquid spray.

The plant-associated microorganisms of the invention can be applied by any conventional method to the surfaces of cereal heads. For example, they can be applied as an aqueous spray or dip, as a wettable powder, or as a dust. However, when preparing dried formulations, rapid drying may decrease efficacy and should be avoided, particularly when formulating the above-mentioned *Pseudomonas* sp. strain. Preferably, the microorganisms of the invention are applied as an aqueous spray on the leaves or to the soil around the cereal plant, or to the seeds by coating the seeds, or in the silo after harvest of the grains.

It is well known in the art that the treatment modalities depend on many conditions such as the culture type, environment, disease to be treated, etc. The skilled in the art is able to determine the proper conditions for use of the composition according to the invention.

Composition

The present invention also provides a phytosanitary composition comprising at least one plant associated microorganism selected from the group consisting of *Pseudomonas trivialis* (PsTri), *Pseudomonas lurida* (PsLu), *Phaeophlebiopsis* sp. (PS), *Periconia macrospinosa* (PM), and combinations thereof, as defined above, in an agronomically acceptable carrier.

In one preferred embodiment, the plant-associated microorganism belongs to the *Pseudomonas trivialis* species.

Accordingly, in a particular embodiment, the plant-associated microorganism is selected from the group consisting of *Pseudomonas trivialis* strains PsTri1, PsTri2, PsTri3, PsTri4, PsTri5, PsTri6, natural variants thereof and combinations thereof. More preferably, the plant-associated microorganism is selected from the group consisting of *Pseudomonas trivialis* strains PsTri1, PsTri2, PsTri3, PsTri4, PsTri5, PsTri6 and combinations thereof. Even more preferably, the plant-associated microorganism is *Pseudomonas trivialis* strain PsTri3 or a natural variant thereof.

In another embodiment, the plant-associated microorganism belongs to the *Pseudomonas lurida* species.

Accordingly, in a particular embodiment, the plant-associated microorganism is selected from the group consisting of *Pseudomonas lurida* strains PsLu1, PsLu2, PsLu3, natural variants thereof and combinations thereof. More preferably, the plant-associated microorganism is selected from the group consisting of *Pseudomonas lurida* strains PsLu1, PsLu2, PsLu3 and combinations thereof. Even more preferably, the plant-associated microorganism is *Pseudomonas lurida* strain PsLu3 or a natural variant thereof.

In another particular embodiment, the plant-associated microorganism is selected from the group consisting of *Pseudomonas trivialis* strains PsTri1, PsTri2, PsTri3, PsTri4, PsTri5, PsTri6, *Pseudomonas lurida* strains PsLu1, PsLu2, PsLu3, natural variants thereof and combinations thereof. More preferably, the plant-associated microorganism is selected from the group consisting of *Pseudomonas trivialis* strains PsTri1, PsTri2, PsTri3, PsTri4, PsTri5, PsTri6, *Pseudomonas lurida* strains PsLu1, PsLu2, PsLu3 and combinations thereof.

Even more preferably, the plant-associated microorganism is selected from the group consisting of *Pseudomonas trivialis* strain PsTri3 and *Pseudomonas lurida* strain PsLu3, and combinations thereof.

In still another embodiment, the plant-associated microorganism belongs to the *Phaeophlebiopsis* sp. species.

Accordingly, in a particular embodiment, the plant-associated microorganism is selected from the group consisting of *Phaeophlebiopsis* sp. strain PS1 and natural variants thereof. More preferably, the plant-associated microorganism is *Phaeophlebiopsis* sp. strain PS1.

In still another embodiment, the plant-associated microorganism belongs to the *Periconia macrospinosa* species.

Accordingly, in a particular embodiment, the plant-associated microorganism is selected from the group consisting of *Periconia macrospinosa* strains PM1, PM2, natural variants thereof and combinations thereof. More preferably, the plant-associated microorganism is selected from the group consisting of *Periconia macrospinosa* strains PM1, PM2 and the combination thereof. Even more preferably, the plant-associated microorganism is *Periconia macrospinosa* strain PM1 or a natural variant thereof.

In another particular embodiment, the plant-associated microorganism is selected from the group consisting of *Phaeophlebiopsis* sp. strain PS1, *Periconia macrospinosa* strains PM1, PM2, natural variants thereof and combinations thereof. More preferably, the plant-associated microorganism is selected from the group consisting of *Phaeophlebiopsis* sp. strain PS1, *Periconia macrospinosa* strains PM1, PM2 and combinations thereof.

Even more preferably, the plant-associated microorganism is selected from the group consisting of *Phaeophlebiopsis* sp. strain PS1, *Periconia macrospinosa* strain PM1, and combinations thereof.

In another particular embodiment, the plant-associated microorganism is selected from the group consisting of *Pseudomonas trivialis* strains PsTri1, PsTri2, PsTri3, PsTri4, PsTri5, PsTri6, *Pseudomonas lurida* strains PsLu1, PsLu2, PsLu3, *Phaeophlebiopsis* sp. strain PS1, *Periconia macrospinosa* strains PM1, PM2, natural variants thereof and combinations thereof. More preferably, the plant-associated microorganism is selected from the group consisting of *Pseudomonas trivialis* strains PsTri1, PsTri2, PsTri3, PsTri4, PsTri5, PsTri6, *Pseudomonas lurida* strains PsLu1, PsLu2, PsLu3, *Phaeophlebiopsis* sp. strain PS1, *Periconia macrospinosa* strains PM1, PM2, and combinations thereof.

Still preferably, the plant-associated microorganism is selected from the group consisting of *Pseudomonas trivialis* strain PsTri3, *Pseudomonas lurida* strain PsLu3, *Phaeophlebiopsis* sp. strain PS1, *Periconia macrospinosa* strain PM1, natural variants thereof and combinations thereof. Even more preferably, the plant-associated microorganism is selected from the group consisting of *Pseudomonas trivialis* strain PsTri3, *Pseudomonas lurida* strains PsLu3, *Phaeophlebiopsis* sp. strain PS1, *Periconia macrospinosa* strain PM1 and combinations thereof.

By "agronomically acceptable carrier" is meant herein a carrier enabling application of the composition on cereal plants and/or grains or seeds and/or soil, during culture or after harvesting, during storage, without inducing adverse effects on the plant and/or on the grain or seed and/or on the soil. Preferably, the agronomically acceptable carrier is compatible with a food use of the plant and/or grain.

The agronomically acceptable carrier according to the invention is typically sterile water, starch, polysaccharides, sodium alginate, cellulose, etc. Formulations designed for these modes of application will usually include a suitable liquid or solid carrier together with other adjuvants, such as wetting agents, sticking agents and the like.

Preferably, the plant-associated microorganism of the invention is present in the composition at a concentration of from $10^1$ to about $10^{13}$ propagules/ml of liquid composition and preferably from $10^2$ to $10^{12}$ propagules/ml of liquid composition, preferably also from $10^3$ to $10^{11}$ propagules/ml of liquid composition, preferably also from $10^4$ to $10^{10}$ propagules/ml of liquid composition, preferably also from $10^5$ to $10^9$ propagules/ml of liquid composition, preferably also from $10^6$ to $10^8$ propagules/ml of liquid composition, preferably also from $10^7$ to $10^8$ propagules/ml of liquid composition.

In a particular yet preferred embodiment, the composition further comprises the microorganisms disclosed by Bujold et al., 2001, Schisler et al., 2002b; da Luz et al., 2003; Gilbert & Fernando, 2004, Schisler et al., U.S. Pat. Nos. 6,562,337 and 6,312,940, and Xue et al., 2009.

Still preferably, the composition further comprises *Clonostachys rosea*, as defined above.

Preferably, the composition comprises *Clonostachys rosea* strain CR at a concentration of from $10^1$ to about $10^{13}$ propagules/ml of liquid composition and preferably from $10^2$ to $10^{12}$ propagules/ml of liquid composition, preferably also from $10^3$ to $10^{11}$ propagules/ml of liquid composition, preferably also from $10^4$ to $10^{10}$ propagules/ml of liquid composition, preferably also from $10^5$ to $10^9$ propagules/ml of liquid composition, preferably also from $10^6$ to $10^8$ propagules/ml of liquid composition, preferably also from $10^7$ to $10^8$ propagules/ml of liquid composition.

The following examples are intended only to further illustrate the invention and are not intended to limit the scope of the invention which is defined by the claims.

EXAMPLE

Figure 1:
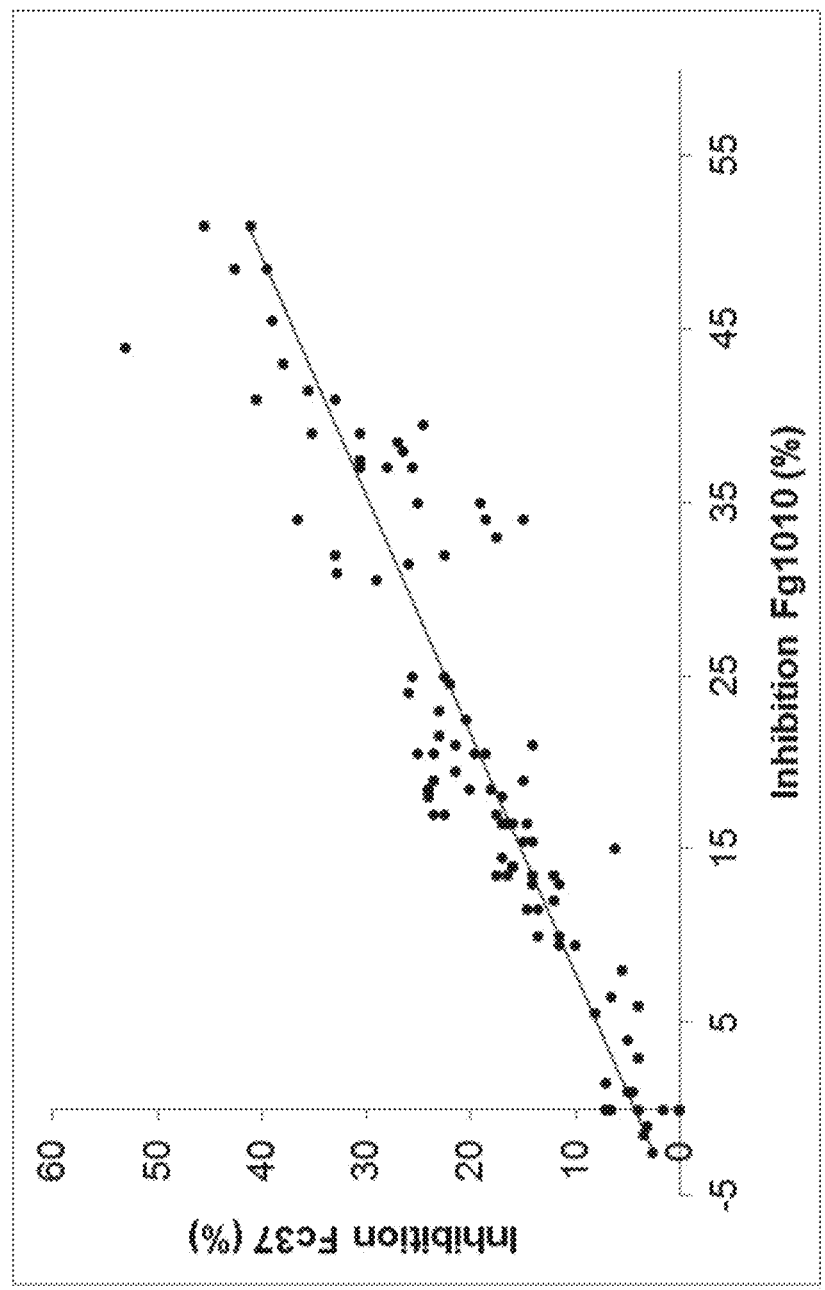
FIG. 1 Correlation (Spearman test) between Inhibition Indexes (Ii) in vitro of both *Fusarium* species (*F. graminearum* strain Fg1010 and *F. culmorum* strain Fc37), for each plant-associated microorganism evaluated. R value near 1 indicates a strong correlation between both variables.

This example shows the ability of strains of *Pseudomonas trivialis*, *Pseudomonas lurida*, *Periconia macrospinosa*, *Phaeophlebiopsis* sp. and *Clonostachys rosea*, isolated from inner tissues of wheat plants, to inhibit the mycelial growth of *Fusarium* spp. in vitro and the ability of a subselection of these strains in planta to reduce *F. graminearum* infection.

Materials and Methods

Sampling

Field samplings were conducted between May and July 2012 at Cucharmoy, France, (48° 35' 00" N 3° 11' 40" E) on untreated experimental plots of Soufflet Agriculture. The preceding crop was peas (*Pisum sativum*) in 2011 and wheat (*Triticum aestivum*) in 2010. Plants from two wheat cultivars Caphorn and Apache, known to differ in their susceptibility to FHB, were collected at heading (GS 59, according to the code defined by Zadoks et al., 1974), flowering (GS 61-69) and mealy ripe (GS 77-79). Apache is more resistant than Caphorn to FHB, with respective resistance levels near seven and three, on the resistance scale to FHB going from 2 (most susceptible cultivar) to 7 (most resistant cultivar). Development stages were chosen as to cover the critical period for infection by FHB, when conidia and ascospores of pathogens could infect the heads. Plots from both cultivars were separated only by a few meters and, therefore, benefitted from the same soil and growth conditions. Four plants from both cultivars were sampled at each stage of development, with Apache developing 2 to 3 days in advance of Caphorn. Due to favorable climatic conditions, fungal diseases could be observed in the experimental plots and sampling plants were chosen that displayed the fewest symptoms of diseases with the hypothesis that plant-associated microorganisms may have protected the plants against the growth or activity of pathogens.

Isolation of Plant-Associated Microorganisms

Two isolation methods have been used: the commonly-used fragments plating method (Carroll & Carroll, *Canadian Journal of Botany* 56, 3034-43, 1978; Carroll, *Ecology* 69, 2-9, 1988) and the high throughput culturing method (Collado et al., *FEMS Microbiology Ecology* 60, 521-33, 2007; Unterseher & Schnittler, *Mycological Research* 113, 645-54, 2009). Four plants, randomly taken from both cultivars at each stage of plant development, were used for each isolation technique. Roots and aerial organs of plants including leaves, stems, glumes (at heading and flowering), anthers (at flowering), kernels (at mealy ripe and on crop residues), were surface-sterilized by dipping them in 70% EtOH for 2 min, in 0.5% NaOCl for 2 min, in 70% EtOH for 1 min and briefly rinsed in sterile distilled water. The method of Schulz et al. (*Defining symbiosis of the endophyte-host interaction. Symbiosis*, Philadelphia, Pa. (USA), 1998) was applied to check the effectiveness of surface sterilization. Then, for the fragments plating technique, five fragments per organ, 25 mm long, were taken from each plant, except for anthers and kernels that were taken entirely. Each fragment (or organ) was cut into four or five pieces inoculated in Petri plates containing malt-agar medium, with five Petri plates per organ for each cultivar at each stage of plant development. For the high throughput culturing technique (HTC), enough plant material to fill a 10 cm petri-dish was first ground in Waring Blender (Waring Laboratory and Sciences, Torrington, CT, USA) with 200 ml of sterile water, for 1 min at maximum speed. For each cultivar, for plants sampled at heading or flowering and for crop residues, only one HTC was performed. For plants sampled at mealy ripe, roots, stems, leaves and kernels from four plants were sorted and each type of organ was processed separately. After grinding, the particle slurry was strained through a stack of three sieves with pore sizes of 1 mm, 210 µm and 105 µm (Spectra Mesh woven filters; Spectrum Labs, Rancho Dominguez, CA). The residues were washed in 1.5 liters of sterile water flowing through the sieve assembly. Particles collected on the 105 µm sieve were suspended in 35 ml of sterile water, centrifugated for 10 min at 1800 g and the dottle was weighed and resuspended in 0.1% aqueous carboxymethyl cellulose (5 ml per gram of particles). The obtained solution was diluted twenty times (the dilution factor was determined as near-optimal in previous experiments) and 5 µl of the final solution for each sample was inoculated per well, of 48-well plates, containing 1 ml of yeast extract medium supplemented with antibiotics (streptomycin and oxytetracyclin, 10 mg ml$^{-1}$) for the isolation of fungi or lysogenic-broth medium for the isolation of bacteria. Twenty 48-well plates were filled for each HTC. Plates were incubated at 25° C. with ambient light and observed daily for fungal and bacterial growth up to two weeks, until plates' invasion. Emergent colonies were picked and transferred on fresh medium for isolation into pure cultures.

Sequencing and Molecular Identification

For fungal isolates, genomic DNA was extracted from fresh mycelium grown on Malt Agar (MA). Extractions were performed using the DNeasy Plant Mini Kit (Qiagen, Ltd., Crawley, UK) following the manufacturer's instructions. ITS plus the 5' end of 28S rDNA were amplified using primers sets ITS4/ITS5 (White et al., *PCR Protocols: a guide to methods and applications* 18, 315-22, 1990) and LROR/LR6 (Vilgalys and Hester, *J Bacteriol.* 172 (8):4238-4246, 1990; Vilgalys and Sun, *Proc Natl Acad Sci USA.* 91 (10):4599-4603, 1994) respectively. PCR amplifications were performed using a BioRad DNA Engine Peltier Thermal cycler with 30 cycles of 30 s at 94° C., 30 s at 55° C. (for ITS4/ITS5 primers), or 50° C. (for LROR/LR6 primers), 40 s at 72° C.; 10 min at 72° C., in a 25 µL reaction mix, containing 12.5 µL genomic DNA (dilution: $10^{-2}$ after extraction), 5 µL PCR Direct Loading Buffer with MgCl$_2$ (Q-Biogen), 0.5 µL dNTPs (6.25 mM, dNTPMix, Q-Biogen),1 µL of each 10 µM primer (Eurogentec), 0.125 µL Taq DNA Polymerase (Q-Biogen, 5 units/µL), and 4.875 µL sterile water.

For bacterial isolates, the 3' end of 16S rDNA was directly amplified from one colony diluted in 1 mL sterile water using primers set 27F/1492R (Wilson et al., *J Clin Microbiol.* 28 (9):1942-1946, 1990). PCR amplifications were performed using a BioRad DNA Engine Peltier Thermal cycler with 5 min at 94° C.; 30 cycles of 60 s at 94° C., 60 s at 53° C., 2 min at 72° C.; 10 min at 72° C., in 50 µL reaction mix, containing 4 µL of bacterial suspension, 10 µL of Green Flexi Buffer (x5, Promega), 3 µL MgCl$_2$ (25 mM, Promega), 0.2 µL dNTPs (25 mM, Q-Biogen), 5 µL of each 2 µM primer (Eurogentec), 0.26 µL Taq DNA Polymerase (Go TaqPromega, 5 units/µL), and 22.34 µL sterile water. PCR products were purified and sequenced by Genoscreen (Lille, France) in both directions to confirm the accuracy of each sequence. Sequences were assembled with Codon Code Aligner v.3.7.1 (Codon Code Corporation), checked by visual inspection of the chromatograms and edited if necessary. Sequences were identified using the BLAST option. Best hits were carefully examined to attribute species names (≥97% of sequence similarities).

Effects of Plant-Associated Microorganisms on the Growth of *Fusarium* Strains by Dual Culture Assays in Vitro Overall 758 microbial isolates have been identified through sequencing and molecular identification and 100 of them, fungi and bacteria, have been selected for in vitro screening based on regulatory, industrial, ecological and marketing constraints, regardless of the host cultivar, host organ or host development stage. These plant-associated microorganisms were tested in vitro by dual culture assays with *F. graminearum* strain Fg1010 (Etablissements J. Soufflet) and *F. culmorum* strain Fc37 (CBS120103) to study their ability to inhibit the mycelial growth of these pathogens. One plant-associated microorganism and one pathogen were inoculated together in a Petri plate, 85 mm of diameter, at same distance from the middle of the plate. PDA (Potato Dextrose Agar, 42 g/L) or PCA (Plate Count Agar, AES 23.5 g/L) agar media were used respectively for fungal or bacterial plant-associated microorganisms screening tests. Fungal strains of plant-associated microorganisms were inoculated as mycelium pellets from 7 days cultures on PDA. Bacterial strains were inoculated as bacterial cells from 7 days cultures on PCA in 7 cm lines. Pathogen strains were inoculated as mycelium pellets from 7 days cultures on PDA or on PCA, depending of the plant-associated microorganism to test (bacteria or fungi), and as a similar mycelial growth of Fg1010 or Fc37 could be observed on both media. After inoculation, plates were incubated at 25° C. and 80% of relative humidity up to 7 days. Each plant-associated microorganism/pathogen combination was set up in duplicates and two independent repetitions of the test were done for each strain. Control plates containing *F. graminearum* and *F. culmorum* alone were done for each repetition of the test. Seven days after inoculation, the growth diameter (ø) of *Fusarium* spp. was measured. Two Inhibition Indexes (Ii) were calculated for each plant-associated microorganism strain, for its ability to inhibit the growth of Fg1010 or Fc37. Ii were calculated following the formula:

$$Ii=[(\emptyset_{Fusarium\ alone}-\emptyset_{Fusarium\ in\ confrontation\ with\ the\ plant-associated\ microorganism})/\emptyset_{Fusarium\ alone}]\times 100$$

where *Fusarium* was either Fg1010 or Fc37. A global Inhibition Score (Is) was determined for each plant-associated microorganism strain as the sum of Inhibition Index values towards both species of *Fusarium* (Is=Ii$_{Fg1010}$+Ii$_{Fc}$37). Depending on the plant-associated microorganism strain, Is may range from 0 (no inhibition for any species of *Fusarium*) to 200 points (100% inhibition of both species of *Fusarium*). Statistical analyses were done using R software. The normality of data was assessed with the Shapiro-Wilk test. Spearman test was used to study the correlation between the level of inhibition of both strains of *Fusarium* spp., Fg1010 and Fc37, for each plant-associated microorganism strain evaluated.

Effects of Plant-Associated Microorganisms on Growth of *F. graminearum* on Wheat Spikelets Bioassays have been conducted on Triticum durum wheat cultivar Miradoux (Florimond Desprez) (Growth Stage 50-59 according to the code defined by Zadoks et al.) grown in greenhouses (15° C. night/20° C. day, photoperiod 16 h day/8 h night and 60% of relative humidity). Microbial strains used for those assays were adjusted to $10^6$ conidia.ml$^{-1}$ or cfu.ml$^{-1}$, respectively for fungal or bacterial strains, from −80° C. stock cultures, in sterile water containing Tween 20 (0.1%), hereafter called water-Tween solution, wT.

Biocontrol Activity of Plant-Associated Microorganisms Against *F. graminearum* on Wheat Spikelets Seven plant-associated microorganism strains were studied in planta. To study the effect of these seven plant-associated microorganism strains to independently control Fg1010 in planta, detached spikelets (24 per treatment) were, as described above, dipped in solutions of plant-associated microorganism strains. Four days after treatment, Fg1010 ($10^5$ conidia.ml$^{-1}$) was spray inoculated on 18 spikelets, 6 spikelets per treatment remaining as control sample. Untreated spikelets and spikelets treated with wT were also inoculated with Fg1010 as negative control treatments. Spikelets treated with Piano® (1/20000) (Bayer CropScience) before the inoculation of Fg1010 were used as positive control treatment. All spikelets were incubated at 15° C. night/20° C. day, photoperiod 16 h day/8 h night and 60% of relative humidity. Seven days after the inoculation of Fg1010, the visual rating of symptoms is conducted. At least three independent repetitions of the test have been conducted.

A scale of visual ratings of symptoms is for example used to evaluate the severity of infection in each spikelet. This scale has typically four levels: level 0=healthy spikelets, level 1=spikelets with early visible necrosis, level 2=spikelets with visible *Fusarium* mycelium, level 3=very infected spikelet with mycelium of *Fusarium* mycelium and presence of sporodochia.

From these scale ratings, a severity index (SI) can typically be calculated using the formula: SI=(n0*0+n1*1+n2*2+n3*3)/N where N is the total number of spikelets by treatment, and n0, n1, n2, n3 is the number of spikelets by treatment with infection levels of 0, 1, 2 or 3 on the rating scale. This severity index therefore translates for each treatment the level of *Fusarium* aggressiveness. The minimum value of the severity index is 0 (obtained when the level 0 of infection is attributed to all the spikelets) and the maximum value is 3 (obtained when the infection level 3 is assigned to all spikelets).

Then a Protection Index was calculated for each treatment, as the ratio of the difference between the presence rate of Fg1010 obtained for untreated spikelets and for this treatment, divided by the presence rate of Fg1010 obtained for untreated spikelets. This Protection Index is indicative of the protection conferred by the treatment towards Fg1010.

Protection index=[(*SINT*−*SIX*)/*SINT*]×100 where SINT corresponds to the severity index obtained for spikelets untreated and inoculated by *F. graminearum*, and SIX is the severity index obtained for samples X having undergone the treatment before the inoculation of the pathogen.

Mann-Whitney test was performed using R software to assess the significance of protection differences obtained between two treatments, considering the independent repetitions done for each treatment. The probability value was set to 5% ($\alpha$=0.05).

Results

Effects of Plant-Associated Microorganisms on the Growth of *Fusarium* Strains in Dual Culture Assays in Vitro Overall 758 microbial isolates have been isolated from aerial organs or roots of two wheat cultivars at different stages of plant development, then identified, and 100 of them, fungi and bacteria, have been selected based on regulatory, industrial, ecological and marketing constraints, regardless of the host cultivar, host organ or host development stage. These 69 bacteria and 31 fungi, representing in total 43 species, have been screened in vitro for their ability to inhibit *Fusarium* spp. by dual culture assays.

Results showed a significant correlation between levels of inhibition of both species of *Fusarium* tested: *F. graminearum* strain Fg1010 and *F. culmorum* strain Fc37 (Spearman rank test R=0.932, P<0.05) (FIG. 1). This correlation allowed the inventors to sum both Inhibition Indexes and express the results in terms of Inhibition Scores (Is=IiFg1010+IiFc37).

Among them, 16 plant-associated microorganisms have been selected, regarding their non-toxicity for animals and human and cereals. Among these 16 plant-associated microorganisms, 5 plant-associated microorganisms were fungi and 11 were bacteria. The species *Clonostachys rosea* (Luongo et al., Biocontrol Science and Technology 15, 229-4, 2005; Xue et al., 2009,) and *Bacillus amyloliquefaciens* (Baffoni et al., BMC Microbiol. 15, 242, 2015) are known to inhibit the growth of *Fusarium* spp.

Table 1 shows the characteristics of 16 plant-associated microorganisms isolated from wheat and used for in vitro screening tests, and in planta tests. The sampling method is either fragments plating (FP) or high throughput culturing (HTC). Type of strains corresponds to fungi (F) or bacteria (B). The host variety is either Apache (A) or Cap Horn (CH). The sampling stage is heading (H), flowering (F), or mealy ripe (MR). The host organs correspond to aerial organs (A) or roots (R). The mention 'ND' for host organs corresponds to samples processed with HTC method at heading, flowering or on crop debris, for which aerial organs and roots were pooled. The growth of plant-associated microorganism strains corresponds to their ability to grow on synthetic media (PDA for yeasts and fungi and PCA for bacteria).

TABLE 1

Characteristics of 16 plant-associated microorganisms isolated from wheat and used for in vitro screening tests, and in planta tests.

| Strain | Species | Sampling method | Type | Host variety | Sampling stage | Host organs | In vitro screening | Wheat detached spikelets screening |
|---|---|---|---|---|---|---|---|---|
| PS1 | Phaeophlebiopsis sp. | HTC | F | CH | MR | A | YES | YES |
| CR | Clonostachys rosea | FP | F | A | H | R | YES | YES |
| PM1 | Periconia macrospinosa | FP | F | CH | MR | R | YES | NO |
| PM2 | Periconia macrospinosa | HTC | F | A | MR | R | YES | NO |
| PsLu3 | Pseudomonas lurida | FP | B | CH | MR | A | YES | YES |
| PsTri3 | Pseudomonas trivialis | HTC | B | CH | MR | A | YES | YES |
| PsTri6 | Pseudomonas trivialis | FP | B | CH | H | R | YES | YES |
| PsLu1 | Pseudomonas lurida | HTC | B | CH | MR | A | YES | NO |
| PsTri4 | Pseudomonas trivialis | FP | B | A | F | A | YES | NO |
| PsTri1 | Pseudomonas trivialis | FP | B | CH | F | A | YES | NO |
| PsLu2 | Pseudomonas lurida | HTC | B | CH | D | ND | YES | NO |
| PsTri2 | Pseudomonas trivialis | FP | B | A | F | A | YES | NO |
| PsTri5 | Pseudomonas trivialis | FP | B | A | F | A | YES | NO |
| Sani3 | Sanguibacter inulinus | HTC | B | A | MR | A | YES | YES |
| CH1 | Cladosporium halotolerans | HTC | F | A | H | ND | YES | YES |
| BaAm | Bacillus amyloliquefaciens | FP | B | CH | MR | A | YES | YES |

Figure 2:
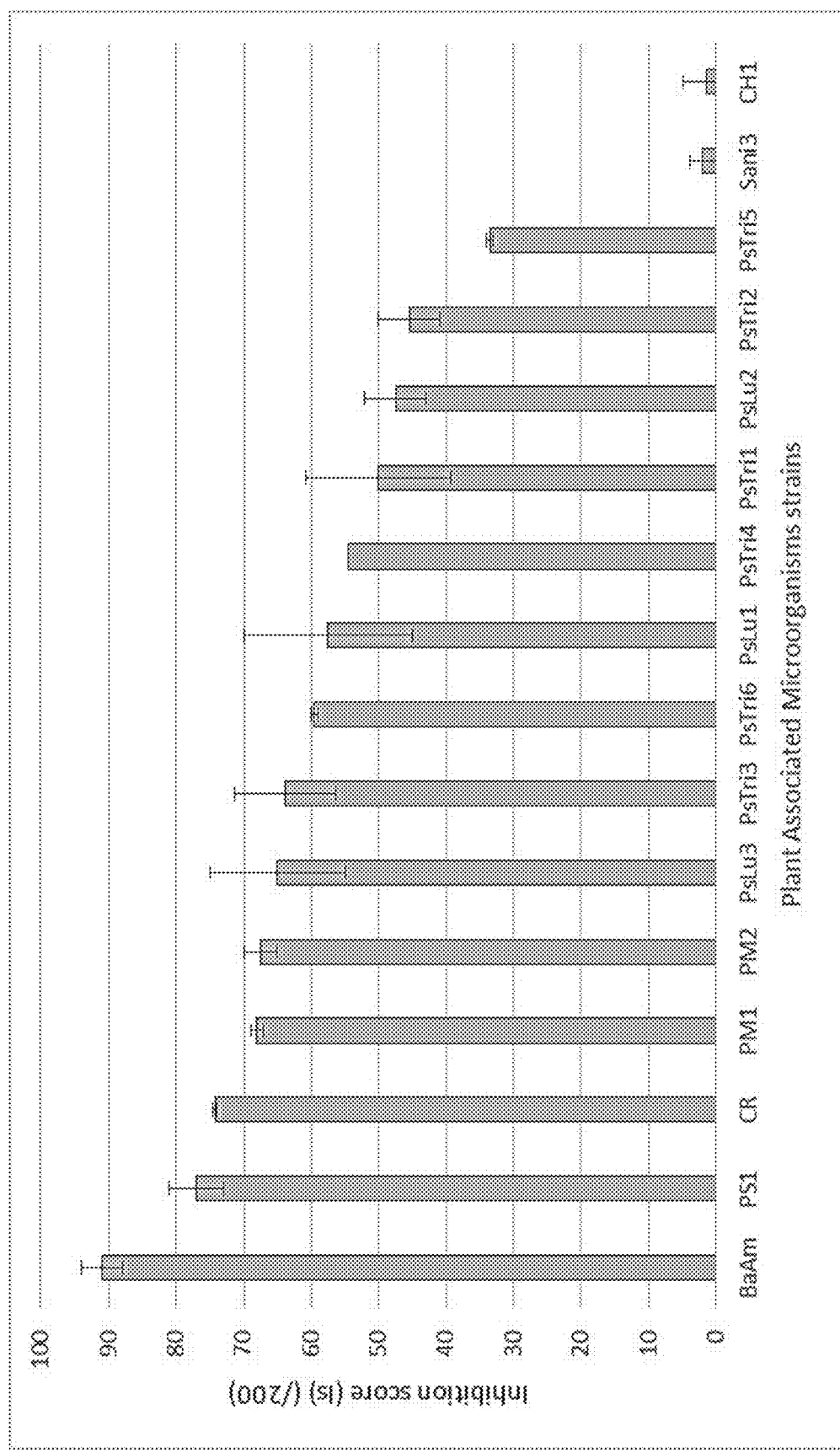
FIG. 2 Inhibition score (Is) towards *F. graminearum* strain Fg1010 and *F. culmorum* strain Fc37 of 16 plant-associated microorganisms isolated from wheat plants tested in vitro by dual cultural assays.

Inhibition score (Is) towards *F. graminearum* strain Fg1010 and *F. culmorum* strain Fc37 of 16 plant-associated microorganisms isolated from wheat plants tested in vitro by dual cultural assays are represented in FIG. 2. A wide range of efficacy was observed among plant-associated microorganism strains in their ability to inhibit in vitro the growth of *Fusarium* spp., with Is ranging from 0 to 45.5% (i.e. 0 to 91 out of 200). Sani3 and CH1, respectively bacterium and fungus, are negative controls. CR and BaAm are positive controls.

Two specific fungal species were identified: *Phaeophlebiopsis* sp. and *Periconia macrospinosa*. *Phaeophlebiopsis* sp. exhibited an Is of 38.5% and *Periconia macrospinosa* exhibited an Is of 33.8 to 34% (34% for the PM1 strain and 33.8% for the PM2 strain). Among bacteria, species belonging to *Pseudomonas*, *Pseudomonas trivialis* and *Pseudomonas lurida*, confer respectively an Is of 16.8 to 31.9% (31.9% for the PsTri3 strain, 29.8% for the PsTri6 strain, 27.3% for the PsTri4 strain, 25% for the PsTri1 strain, 22.8% for the PsTri2 strain and 16.8% for the PsTri5 strain) and of 23.8 to 32.5% (32.5% for the PsLu3 strain, 28.8% for the PsLu1 strain and 23.8% for the PsLu2 strain). It should however be noted that some *Pseudomonas* species such as *Pseudomonas fluorescens*, *Pseudomonas helvolus* or *Pseudomonas libanensis* displayed a very low IS inferior to 15%.

Effects of Plant-Associated Microorganisms on *F. graminearum* on Detached Spikelets Based on their high Is against *Fusarium* in vitro (Is>30%), three strains have been selected to conduct in planta bioassays, focusing on the species easy to grow on synthetic media and retaining only the strain with the highest Is per species. In this way, *P. trivialis* strain PsTri3, *P. lurida* strain PsLu3 and *Phaeophlebiopsis* sp. strain PS1 have been selected. Two strains with very low Is in vitro, *Sanguibacter inulinus* strain Sani3 and *Cladosporium halotolerans* strain CH1 have also been selected as biological negative controls. *Bacillus amyloliquefaciens* strain BaAm and *Clonostachys rosea* strain CR are used as positive controls.

The selected plant-associated microorganism strains have been inoculated on wheat spikelets and Fg1010 was inoculated 4 days later.

Figure 3:
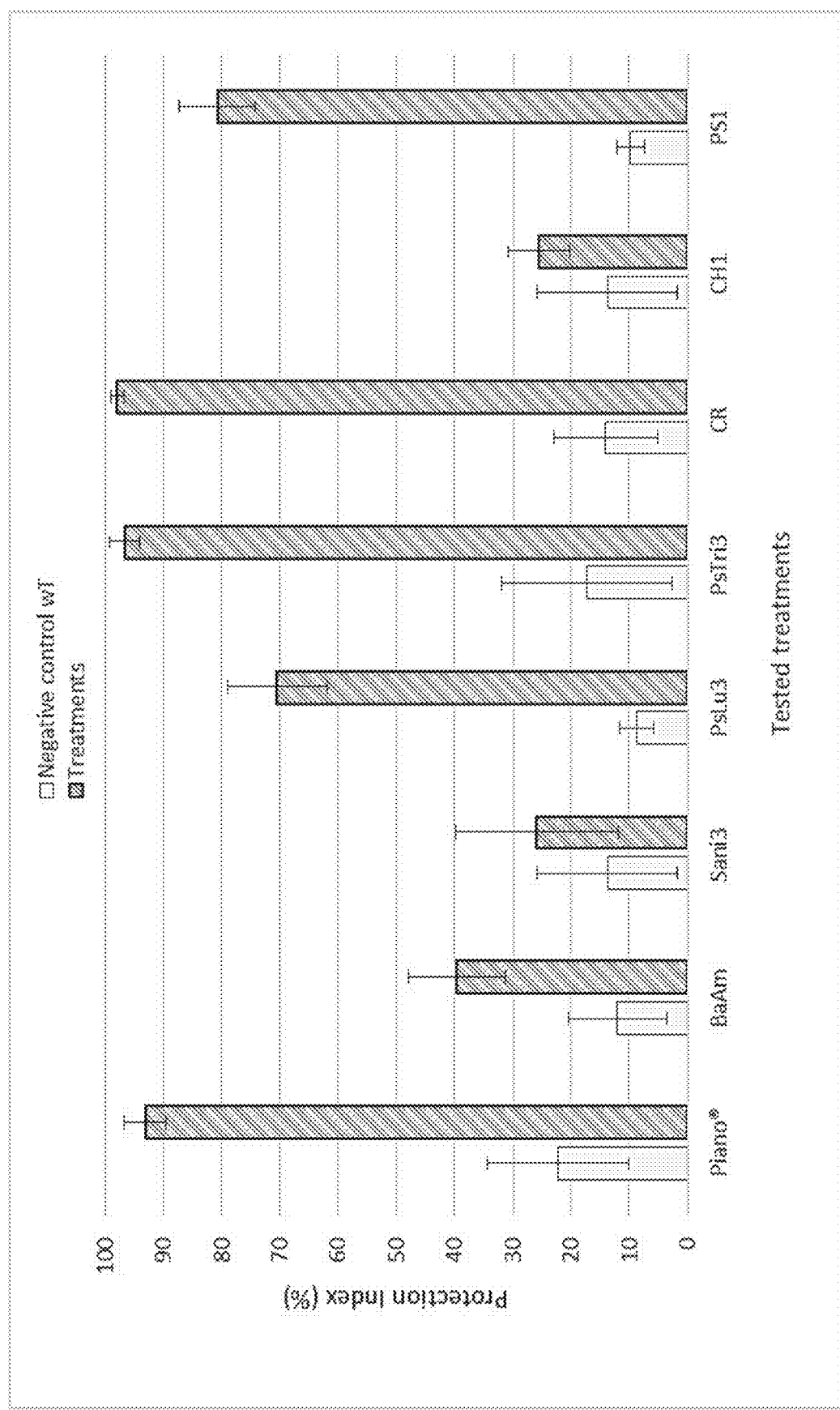
FIG. 3 Protection index conferred against *F. graminearum* strain Fg1010 by all tested treatments, 7 days after the inoculation of the pathogen. The fungicide Piano® (Bayer CropScience) represents the positive control treatment. Each treatment (strains and fungicide Piano®) is presented in relation to the Water-Tween solution (wT) (negative control treatment) performed in the same experiments, i.e. the value of wT for each treatment is calculated from the repetitions where the considered treatment is also used. Error bars indicate the standard error of protection indices between 3 to 14 independent repetitions of the test.

The three strains, PsTri3, PsLu3 and PS1 significantly reduced *F. graminearum* growth compared to control spikelets treated with wT. PS1 exhibited a Protection Index of 80.7%, PsLu3 of 70.4% and PsTri3 of 96.6%. The strains PsTri3 and CR exhibited a similar effect than the positive control fungicide Piano® (Bayer CropScience) to reduce the disease (FIG. 3).

These results thus show the interest of *Pseudomonas trivialis* (PsTri), *Pseudomonas lurida* (PsLu), *Phaeophlebiopsis* sp. (PS) *Periconia macrospinosa* (PM), and of *Clonostachys rosea* strain CR for preventing or treating FHB.

The invention claimed is:

1. A method for preventing and/or treating *Fusarium* head blight in a cereal plant and/or cereal grain, comprising a step of applying an effective amount of at least one plant-associated microorganism to said plant, to the soil around said plant or to the seed or grain of said plant, wherein said at least one plant-associated microorganism is selected from the group consisting of
   (i) the *Pseudomonas trivialis* strain PsTri1 deposited under the Budapest Treaty with the Centralbureau voor Schimmelcultures (CBS, Uppsalalaan 8, 3584 CT Utrecht, Netherlands) under Accession number CBS 141 431,
   (ii) the *Pseudomonas trivialis* strain PsTri2 deposited under the Budapest Treaty with the Centralbureau voor Schimmelcultures (CBS, Uppsalalaan 8, 3584 CT Utrecht, Netherlands) under Accession number CBS 141 432,
   (iii) the *Pseudomonas trivialis* strain PsTri3 deposited under the Budapest Treaty with the Centralbureau voor Schimmelcultures (CBS, Uppsalalaan 8, 3584 CT Utrecht, Netherlands) under Accession number CBS 141 433,
   (iv) the *Pseudomonas trivialis* strain PsTri4 deposited under the Budapest Treaty with the Centralbureau voor Schimmelcultures (CBS, Uppsalalaan 8, 3584 CT Utrecht, Netherlands) under Accession number CBS 141 434,
   (v) the *Pseudomonas trivialis* strain PsTri5 deposited under the Budapest Treaty with the Centralbureau voor Schimmelcultures (CBS, Uppsalalaan 8, 3584 CT Utrecht, Netherlands) under Accession number CBS 141 435, (vi) the *Pseudomonas trivialis* strain PsTri6 deposited under the Budapest Treaty with the Westerdjik Fungal Biodiversity Institute (CBS, Uppsalalaan 8, 3508 AD Utrecht, Netherlands) under Accession number CBS 142 248, and (vii) a combination of the strains PsTri1, PsTri2, PsTri3, PsTri4, PsTri5 and PsTri6.

2. The method according to claim 1, wherein the at least one plant associated microorganism is applied in combination with *Clonostachys rosea* strain CR deposited under the Budapest Treaty with the Centralbureau voor Schimmelcultures (CBS, Uppsalalaan 8, 3584 CT Utrecht, Netherlands) under Accession number CBS 141 426.

3. The method according to claim 1, wherein the cereal is wheat or barley.

4. The method according to claim 1, wherein said at least one plant associated microorganism is applied on the leaves of said cereal plant.

5. The method according to claim 1, wherein said at least one plant associated microorganism is applied to the soil around said cereal plant.

6. The method according to claim 1, wherein said at least one plant associated microorganism is applied to the cereal seed or grain.

7. The method according to claim 6, wherein said at least one plant associated microorganism is applied to said cereal grain after harvesting and/or during the storage.

8. The method according to claim 3, wherein said at least one plant associated microorganism is applied as a liquid spray.

\* \* \* \* \*